(12) United States Patent
Blanton (10) Patent No.: US 7,699,799 B2
(45) Date of Patent: Apr. 20, 2010

(54) ULTRASONIC MATERIAL REMOVAL SYSTEM FOR CARDIOPULMONARY BYPASS AND OTHER APPLICATIONS

(75) Inventor: Jared Colin Blanton, Mill Valley, CA (US)

(73) Assignee: Ceeben Systems, Inc., Oakland, CA (US)

(*) Notice: Subject to any disclaimer, the term of this patent is extended or adjusted under 35 U.S.C. 154(b) by 356 days.

(21) Appl. No.: 11/463,121

(22) Filed: Aug. 8, 2006

(65) Prior Publication Data

US 2007/0045188 A1 Mar. 1, 2007

Related U.S. Application Data

(60) Provisional application No. 60/711,386, filed on Aug. 26, 2005.

(51) Int. Cl.
*A61M 37/00* (2006.01)

(52) U.S. Cl. .................................... 604/6.08

(58) Field of Classification Search ............. 604/4.01, 604/5.01, 5.02, 5.04, 6.01, 6.02, 6.03, 6.04, 604/6.08, 6.09, 6.1, 6.11, 6.12, 6.13, 6.14, 604/6.15, 7, 8, 19, 20
See application file for complete search history.

(56) References Cited

U.S. PATENT DOCUMENTS

| | | | |
|---|---|---|---|
| 3,505,988 A | 4/1970 | Deane | |
| 3,698,396 A | 10/1972 | Katemdahl et al. | |
| 3,927,980 A | 12/1975 | Leonard | |
| 4,112,773 A * | 9/1978 | Abts ........................... | 73/642 |
| 4,356,826 A | 11/1982 | Kubota | |
| 4,445,500 A | 5/1984 | Osterholm | |
| 4,450,841 A | 5/1984 | Osterholm | |
| 4,820,260 A * | 4/1989 | Hayden ..................... | 604/6.02 |
| 4,883,459 A | 11/1989 | Calderon | |
| 4,904,237 A | 2/1990 | Janese | |
| 4,963,130 A | 10/1990 | Osterholm | |
| 5,022,899 A | 6/1991 | Hohlfeld et al. | |
| 5,122,267 A | 6/1992 | Giovanetti et al. | |

(Continued)

FOREIGN PATENT DOCUMENTS

WO    WO 01/39819 A2    6/2001

(Continued)

OTHER PUBLICATIONS

Davison et al.; Epidural cooling for regional spinal cord hypothermia during thoracoabdominal aneurysm repair; J. Vasc. Surg.; vol. 20(2); No. 304-10; Aug. 1994 (Abstract Only).

*Primary Examiner*—Manuel A Mendez
(74) *Attorney, Agent, or Firm*—Townsend and Townsend and Crew LLP (57) ABSTRACT

Devices, systems, and methods manipulate target materials within fluids, and may be useful for removing microbubbles and other materials from blood. Ultrasound or acoustic filtering waves may be directed across a flow of blood, and differences in density between the target microbubbles and the blood may enhance separation by driving the lighter matter upward for removal from the blood stream. A disposable acoustically transmissive conduit can replaceably engage an ultrasound transmitter to facilitate sterilization. Exemplary conduits have elongate lumen cross-sections and an axial path resembling a portion of a Mobius strip.

12 Claims, 5 Drawing Sheets

U.S. PATENT DOCUMENTS

| | | | |
|---|---|---|---|
| 5,141,493 A | 8/1992 | Jacobsen et al. | |
| 5,149,321 A | 9/1992 | Klatz et al. | |
| 5,261,874 A * | 11/1993 | Castle | 604/6.08 |
| 5,344,136 A | 9/1994 | Capdeboscq | |
| 5,380,160 A | 1/1995 | Chen | |
| 5,554,280 A | 9/1996 | Loehr | |
| 5,562,821 A | 10/1996 | Gutierrez-Collazo | |
| 5,665,227 A | 9/1997 | Watt | |
| 5,730,720 A | 3/1998 | Sites et al. | |
| 5,811,658 A * | 9/1998 | Van Driel et al. | 73/19.02 |
| 6,254,567 B1 | 7/2001 | Treu et al. | |
| 6,379,331 B2 | 4/2002 | Barbut et al. | |
| 6,409,699 B1 | 6/2002 | Ash | |
| 6,436,295 B2 | 8/2002 | Kim | |
| 6,497,721 B2 | 12/2002 | Ginsburg et al. | |
| 6,743,218 B2 | 6/2004 | Maginot et al. | |
| 6,953,438 B2 * | 10/2005 | Milo | 601/2 |
| 2002/0033181 A1 | 3/2002 | Groth et al. | |
| 2004/0193098 A1 | 9/2004 | Wentling et al. | |
| 2005/0177212 A1 | 8/2005 | Njemanze | |
| 2006/0161107 A1 | 7/2006 | Mantle | |
| 2007/0106247 A1 | 5/2007 | Burnett et al. | |

FOREIGN PATENT DOCUMENTS

| | | |
|---|---|---|
| WO | WO 01/58509 A1 | 8/2001 |

* cited by examiner

ULTRASONIC MATERIAL REMOVAL SYSTEM FOR CARDIOPULMONARY BYPASS AND OTHER APPLICATIONS

CROSS-REFERENCES TO RELATED APPLICATIONS

This application claims the benefit of U.S. Patent Application No. 60/711,386 filed on Aug. 26, 2005, and entitled "Ultrasonic Gas Removal System for Cardiopulmonary Bypass," the full disclosure of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention is generally related to devices, systems, and methods for manipulating materials within and/or separating materials from fluids. In exemplary embodiments, the invention provides an acoustic or ultrasound filter for removal of microbubbles or other target matter from a fluid, particularly for target matter having acoustic impedances and/or densities which are significantly different than that of the remaining fluid. Separation of microbubbles and other matter from biological fluids can be (for example) beneficial for removing microbubbles from blood before introduction of the filtered blood into the patient during cardiopulmonary bypass systems, when using cell-saver systems that filter and return blood that might otherwise be lost during surgery, for dialysis treatment, and the like.

A number of different types of treatments rely on external processing of the blood of a patient. An example of external blood processing is often included in heart surgeries that involve cardioplegia, in which beating of the heart is temporarily halted. During cardioplegia, pumping of the blood through the vascular system, and re-oxygenating the blood can be performed outside the patient's body by a heart-lung machine of a cardiopulmonary bypass system. While the patient is relying on the cardiopulmonary bypass system, the blood flows in a continuous stream from the patient, through the heart-lung machine, and back into the patient. Similarly, patients with compromised kidney function rely on dialysis treatments in which the blood flows from the patient, through the dialysis machine, and back into the patient.

In general, biological fluids that are to be introduced into a patient are handled and processed with great care. This can be relatively challenging during dialysis treatments, cardiopulmonary bypass, and other procedures in which a stream of fluids are removed from the body, processed outside the body, and reintroduced into the body. Such treatments often involve filtration, gas exchange, and the like, with the biological fluid passing through pumps, tubing, filter media, and other artificial structures. Bubbles of various sizes can be introduced into the biological fluids by this processing. While removal of larger bubbles can be relatively straightforward, it can be quite challenging to effectively remove microbubbles from blood and other biological fluids prior to introduction into a patient. Small particulates (and other undesirable materials that are difficult to remove) may also be inadvertently introduced into blood during processing.

While a variety of techniques have been proposed and/or implemented for removal of microbubbles and other impurities from blood and other biological fluids, many known filtration techniques have generally been found to be less than ideal. Hence, it would generally be desirable to provide improved devices, systems, and methods for manipulation and/or separation of target materials from within fluids, particularly from biological fluids. It would be particularly desirable if these improved techniques were compatible with existing biological fluid processing or even facilitated improved biological fluid processing to enhance the safety and efficacy of dialysis treatments, heart-lung machines, and the like. Ideally, such improved techniques would not significantly increase the complexity or cost of the existing blood (and other biological fluid) processing systems, nor increase the difficulty in sterilizing biological fluid processing systems.

BRIEF SUMMARY OF THE INVENTION

The present invention generally provides improved devices, systems, and methods for manipulating target materials within and/or separating target materials from fluids, particularly from biological fluids. Embodiments of the invention may be useful for removing microbubbles and other acoustically manipulatable (and often embolizable) materials from blood, particularly for treatments involving cardiopulmonary bypass, dialysis treatments, and the like. When used for filtration of blood or other biological fluids, embodiments of the invention may benefit from a mismatch of acoustic impedance between the (and from differences in density between) the target matter (such as microbubbles, microspheres, microbeads, or the like) and the remaining biological fluids, with exemplary embodiments employing waves of acoustic or ultrasound energy sweeping upward across a stream of the biological fluid so that acoustic filtering and gravity together drive a lighter target matter upward for easy removal from the fluid stream. A disposable conduit that is at least in part acoustically transmissive can acoustically couple the fluid stream to an ultrasound transmitter, facilitating sterilization of the system by replacement of the conduit. An exemplary laminar-flow conduit has an elongate cross-section, ideally with a height (in the upward direction traveled by the propagating waves) which is significantly greater than a width across the conduit. Deleterious reflection of the waves can be inhibited by a sufficient match between the acoustic impedance of the conduit material opposite the transducer and the biological fluid, by controlling the angle at which the waves from the biological fluid impinge on the conduit material, and the like. An exemplary conduit in which filtration takes place has a path resembling a portion of a Mobius strip, providing a balanced flow resistance across the conduit lumen and allowing removal of the target matter from an at least local maximum height within the lumen.

In a first aspect, the invention provides a filter for separating a target matter from a fluid flow. The filter comprises a fluid conduit having an input for receiving the fluid flow, an output, and a lumen defining a fluid flow path from the input to the output. An ultrasound or acoustic transmitter can generate ultrasound or acoustic waves. A target matter port is in fluid communication with the conduit lumen. The transmitter is oriented so that the waves drive the target matter across the fluid flow path toward the port.

In many embodiments, the fluid flow at the input will include the target matter and a biological fluid. The target matter will often be less dense than the fluid, and the transmitter can be disposed below the fluid flow path. The port may open to the lumen from above the fluid flow path, allowing the less dense target matter to be removed from the top of the biological fluid so that gravity aids in separation and removal of the target matter.

The fluid conduit can have an upper surface which, in the direction along the fluid flow path, slopes upward toward the port. After passing the port, the upper surface may then slope downward away from the port. Hence, gravity may further tend to urge microbubbles and other low density target matter upstream and/or downstream toward the port. Regardless of the orientation, an elongate lumen cross-section may extending in the direction of the wave propagation may enhance filter efficiency and/or effectiveness.

The fluid path resistance across the lumen can be balanced to facilitate separation. For example, the lumen may define a portion of a Mobius-strip-like structure, having an axis that includes at least 180° of axial twist along the flow path. This axial twisting (often again with an elongate lumen cross-section) may be defined by channels in a stack of plates, by twisting a flexible conduit about it axis, or the like. The fluid path will preferably comprise a laminar fluid path, and the port will be included within a bifurcation having an acute angle between the target matter flow path (along a target matter lumen) and the fluid flow path.

The conduit will often comprise a material having an acoustic impedance that sufficiently matches an impedance of the fluid flow to inhibit reflection of the waves when the waves from the biological fluid impinge on the conduit. For example, the conduit material may have a Rayles number that is within about 15% of the Rayles number of the biological fluid, ideally being within about 10% of the Rayles number of the biological fluid. Where the biological fluid comprises blood, suitable materials for including in the conduit may have an acoustic impedance of between about 1.2 MRayle and 1.7 MRayle, with exemplary materials comprising an ultrasound probe head material, a polymethyl pentane such as TPx (which may be commercially available from Mitsubishi Corp. of Japan), HDPE, or UHDPE. Reflection of the waves may also be inhibited by controlling the angle at which the waves from the biological fluid strike the conduit, with exemplary embodiments having waves striking the conduit at close to about 90°, such as between about 80 and 110°.

The transmitter may be attached to a structure having a receptacle which removably receives the conduit, and which maintains acoustical coupling between the transmitter and conduit. While some embodiments may employ a fluid bath encompassing the conduit and at least a portion of the transmitter and/or openings in the conduit to directly expose the transducer surface to the fluid flow, exemplary embodiments may rely on simple engagement between a flexible conduit material and the transducer surface to facilitate removal and replacement of the conduit so as to avoid cross-contamination of sequential fluid flows and decrease the need for costly sterilization. Such coupling may optionally be enhanced by a gel at the interface between the transmitter and the conduit material.

While a variety of standard wave forms might be employed to sweep the target matter from the stream of fluid, exemplary embodiments may employ non-standard complex waveforms to drive the transmitter. For example, rather than a simple standard sign wave, a square wave, a triangular wave, or the like, tailored waveforms having multiple changes in curvature (such as a waveform that undergoes a plurality of changes between a positive second derivative and a negative second derivative) as the wave advances between a minimum and maximum amplitude within a single cycle. Waveforms generated by a less than 25% duty cycle (such as a waveform generated by a 10% duty cycle) may also be employed. Varying or sweeping of the ultrasound frequency may also be employed to inhibit the formation and/or deleterious effects of standing waves.

The target matter may comprise gas bubbles such as microbubbles or the like, and the fluid flow may comprise blood flow. Alternative embodiments may filter microspheres, polymer or other beads, or the like from biological or other fluids, and/or may manipulate these target tissues within biological or other fluids.

In another aspect, the invention provides a method for filtering a biological fluid. The method comprises flowing the fluid along a fluid flow path. Target matter is driven from within the flowing fluid towards a target matter port by directing ultrasound or acoustic waves across the fluid flow path. The target matter is removed from the fluid flow path through the port.

DETAILED DESCRIPTION OF THE INVENTION

The present invention generally provides improved devices, systems, and methods for manipulating target materials within fluids and/or separating those target materials from fluids. Advantageous embodiments allow filtration of acoustically manipulatable or low-density materials (such as bubbles, microbubbles, microspheres, beads, microbeads, and/or the like) from blood or other biological fluids. Exemplary embodiments use acoustic or ultrasound waves to drive microbubbles across a flow of blood within a conduit and towards a target matter removal port. Hence, aspects of the invention may have applications for removing gaseous bubbles or microparticulates during cardiopulmonary bypass, dialysis treatments, cell savers blood scavenging and separation for return to the patient during surgery, as a supplemental system for catheters, during femoral artery to femoral artery (sometimes referred to as "fem-fem") bypass procedures, during known or newly developed blood filtration (including custom filtration) treatments, and the like. Additional embodiments may be used for filtration of other fluids, including medications or the like. Still further alternative embodiments may be used during filtration of other fluids, such as removal of microbubbles from industrial fluids.

Figure 1:
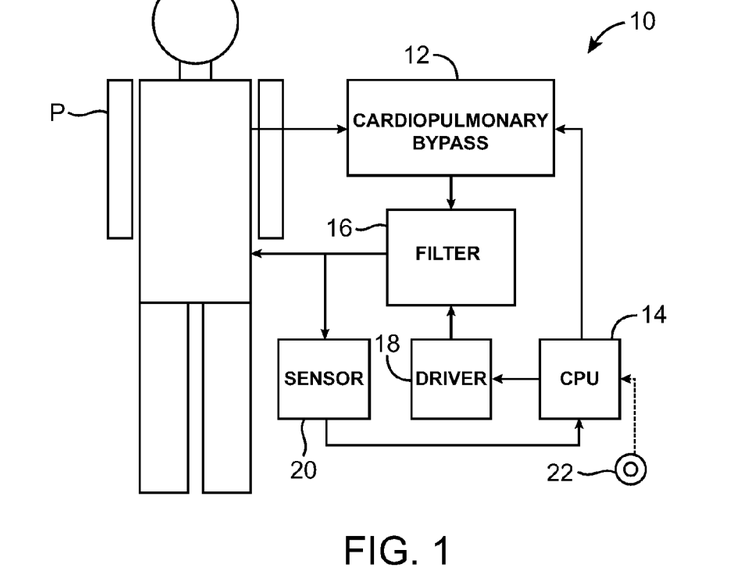
FIG. 1 schematically illustrates a cardiopulmonary bypass system including an embodiment of a filter of the present invention.

Referring now to FIG. 1, an exemplary cardiopulmonary bypass system 10 may include a heart-lung machine 12 for pumping and oxygenation of blood from a patient P. Blood from the patient P enters the heart-lung machine, which generally operates under the control of a controller 14. As a result of the processing of the blood within heart-lung machine 12, the blood leaving the heart-lunch machine may include gaseous microbubbles and/or other embolized microparticulates.

Before the blood from heart-lung machine 12 is reintroduced into patient P, the blood passes through a filter 16. Filter 16 generally makes use of acoustic or ultrasound waves to drive microbubbles and/or particulates across a flow of the blood toward a target matter removal port, with the waves being generated by a transmitter energized by a driver 18 under the control of controller 14. While schematically shown in FIG. 1 as being separate from heart-lung machine 12, filter 16 may be incorporated into heart-lung machine 12 of cardiopulmonary bypass system 10. Alternatively, the individual components of heart-lung machine 12 may be separated into a variety of alternative fluid path structures. Optionally, a sensor 20 determines the efficacy of filter 16 and/or cardiopulmonary bypass system 10, providing feedback signals to the processor 14 of the system.

Processor 14 will typically comprise digital and/or analog data processing circuitry, often including the electronic hardware and/or computer programming software. Suitable hardware may include a general purpose personal computer, workstation, or the like, or may include a specialized proprietary processor or processor board. The hardware of processor 14 will often be combined with software in the form of machine-readable programming instructions or code for implementing one, some, or all of the methods described herein. The code will often be embodied in a tangible media such as a memory, a magnetic recording media, an optical recording media 22, or the like, and/or may be transmitted to processor 14 as electrical signals, optical signals, wireless data signals, or the like. Data and code transmission may be implemented via a cable, an Intranet, an Internet, a wireless network, or the like. Processor 14 will often have or be coupled to appropriate input and output devices for communications between the processor and the user, such as a keyboard, mouse, touchscreen display or other user interface for communications with a user of cardiopulmonary bypass system 10.

Figure 2:
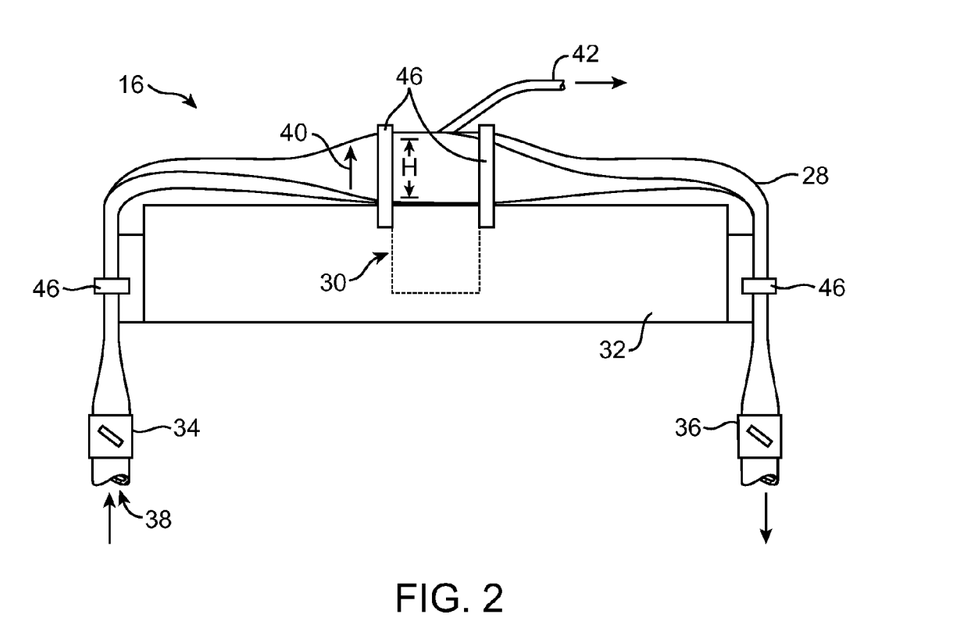
FIG. 2 is a side view showing an exemplary filter for the system of FIG. 1.

Referring now to FIG. 2, an exemplary filter 16 includes a conduit 28 held in place relative to an ultrasound transmitter 30 by a support structure 32. Conduit 28 includes an input end 34 coupled to an output end 36 by a lumen 38. Blood flows into input end 34 from heart-lung machine 12, and flows out from output end 36 toward the patient P. The input and output ends may include couplers such as Luer fittings or the like. Conduit 28 may comprise any of a wide range of polymer or other materials, with lumen 38 optionally having one or more coatings to inhibit deleterious interaction between the bloodstream and the surrounding conduit material. Conduit 28 may, for example, comprise a cast, molded, or extruded TPx, high-density polyurethane, or ultra high density polyurethane.

Exemplary conduit 28 shown in FIG. 2 has a form that is described herein as resembling a portion of a Mobius strip. In general, the lumen within conduit 28 will promote laminar flow of the bloodstream, at least adjacent ultrasound transmitter 30. Such laminar flow can be promoted in a variety of different ways, such as by providing appropriate luminal surface shapes for the Reynolds number of the blood flow that will pass therethrough by providing sufficiently smooth luminal surfaces, transitions, and the like. The lumen adjacent transmitter 30 will typically have a height H which is significantly greater than the luminal width, the height typically being at least two times the luminal width, often being at least four times the luminal width at the transmitter. The exemplary Mobius filter structure has an axial twist of about 90° between the inlet end 34 and transmitter 30, and another axial twist of about 90° between transmitter 30 and the output end 36. This can help balance the flow resistance across the lumen. Also, filter 28 will often be positioned so that an upward orientation 40 of the lumen adjacent transmitter 30 helps urge microbubbles toward a target filter matter port and associated target matter lumen 42. By sufficiently aligning the direction of the applied acoustic force upon the target mater with the direction of the buoyant force on the target matter, separation can be enhanced. Gravity forces on the target material may be opposed to the buoyant force, and both drag and flow may be at least partially perpendicular to the buoyant force. The exemplary Mobius filter has an upper luminal surface that slopes upward prior to adjacent transmitter 30, and then slopes downward after transmitter 30 (as can be understood with reference to FIGS. 2 and 3). Alternative conduit shapes, cross sections, and flow paths may also be used, including non-twisting, locally peaking channels.

In operation, the waves directed from transmitter 30 drive microbubbles 54 upward and toward a target matter port 44 for extraction from lumen 38 via a target matter lumen 42. Ultrasound transmitter 30 may comprise any of a wide variety of commercially available ultrasound transmitting structures, including transducers having transmitting and receiving capabilities. One exemplary transmitter comprises a 1" diameter (optionally having a 2" diameter) ceramic ultrasound transducer commercially available from Channel Industries, Inc. of Santa Barbara, Calif. under the model name Navy III™ 5800 PZT 1 MHz transducer. This exemplary transducer may, for example, transmit ultrasound waves at 1 MHz or less, with the effective size of the transmitting surface often being less than the overall transducer size (the primary mode of the transducer often comprising about the center ⅔rds of the overall transducer radius). One MHz ultrasound energy may have a wavelength of about 1.4 mm in blood, with lower wavelengths generally providing better filtering performance. Driving such a transducer at lower frequencies, such as at about 580 kHz, may improve filtering effect, while altering, varying, and/or sweeping the driving frequency can inhibit standing waves and improve the overall capabilities of the filter. Relatively large transmitting surfaces may transmit waves more uniformly across lumen 38, inhibiting deleterious reflection of the waves by limiting an angle at which the waves propagating through the lumen strike the luminal wall of conduit 28. Deleterious reflection of the waves may also be inhibited by sufficiently matching acoustic impedance of the conduit material to that of the fluid within in the lumen. For example, suitable materials for a blood filtering may have an acoustic impedance in a range of from numbers of about 1.2 MRayle to about 1.7 MRayle.

A variety of structures and approaches may be employed to provide acoustic coupling between transmitter 30 and the blood flow within conduit 28. In the exemplary embodiment, support 32 includes a plurality of arms 46 that hold conduit 28 in position with the conduit acoustically coupled to transmitter 30. Advantageously, arms 46 of support structure 32 may replaceably hold conduit 28 in acoustic engagement with transmitter 30. Specifically, inner surfaces of the arms 46 may each define receptacles, with the receptacles together sufficiently supporting and positioning the conduit for use. Removal and replacement of conduit 28 between treatment of different patients may help avoid cross-contamination. Arms 46 may be, for example, movable relative to the conduit to facilitate replacement of conduit 28 with a different conduit for treatment of another patient. In other embodiments, the conduit may deform sufficiently to be held by detents of the arms, the arms being fixed. A wide variety of alternative receptacle surface structures might also be employed, including structures which support the conduit using fasteners (such as threaded fasteners or the like) latches, or the like. Optionally, a fluid tank similar to that described in U.S. Pat. No. 5,344,136, the full disclosure of which is incorporated herein by reference, may enhance acoustic coupling by including at least a portion of the transducer surface and conduit in a fluid bath, although such coupling may instead be accomplished without a fluid bath by direct engagement between conduit 28 and transducer 30, by a gel at the conduit/transducer interface, or the like.

Figure 3:
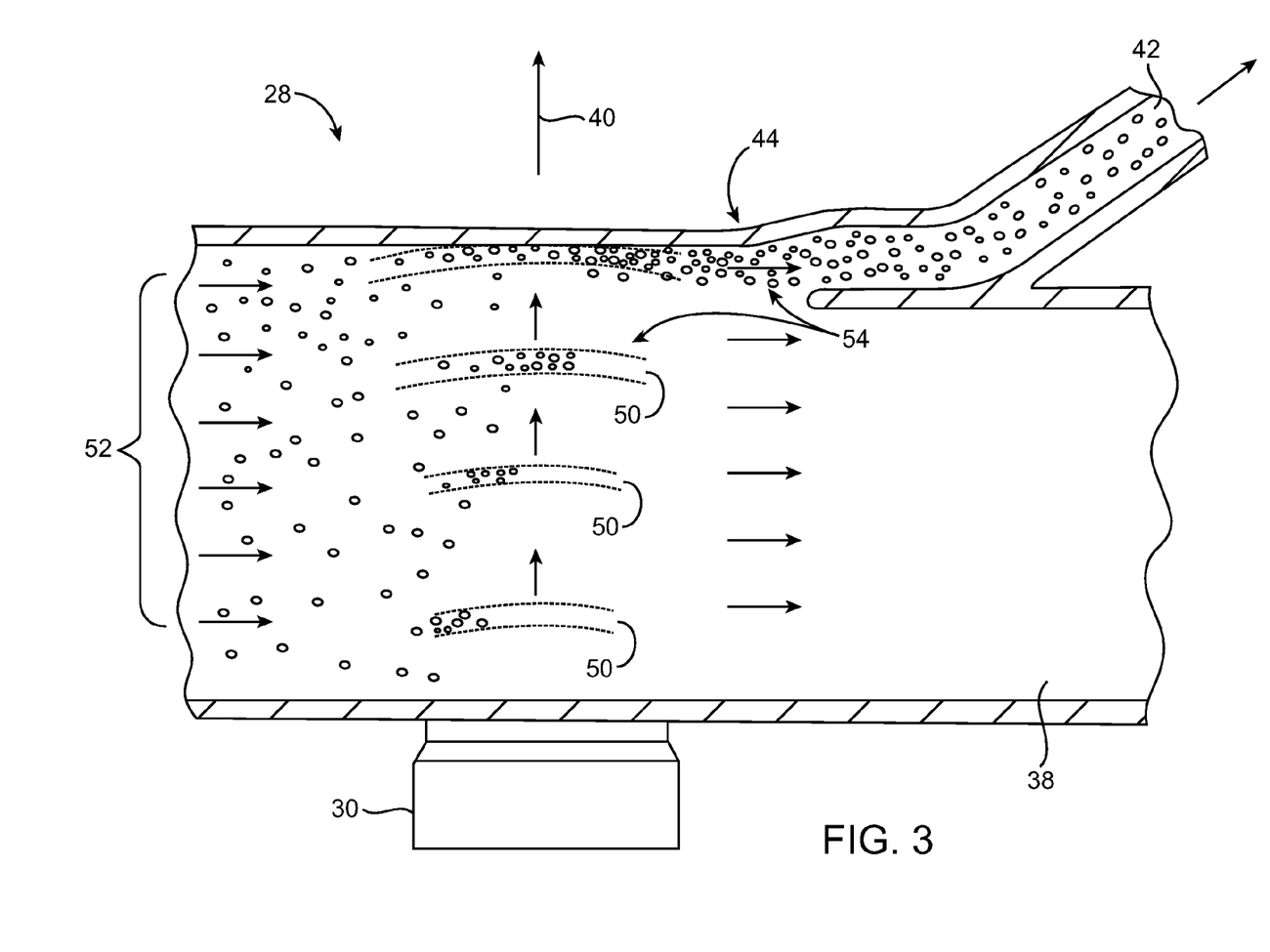
FIG. 3 is a cross-sectional view within the filter of FIG. 2, showing gravity-assisted ultrasound waves driving microbubbles upward within a conduit from a blood flow path.

Removal of microbubbles from the bloodstream within conduit 28 can be understood with reference to FIGS. 2 and 3. Waves 50 propagate through laminar flow 52 of the blood through lumen 38. Aided by gravity, waves 50 drive microbubbles 54 upward across the flow within lumen 38. Drawing the target matter through target matter lumen 42 with a speed sufficient to roughly matching the flow velocities at the entrance of the target matter lumen with that of the flow in lumen 38 may help maintain laminar flow adjacent target matter port 44. Laminar flow may also be maintained by providing a relatively narrow bifurcation angle adjacent port 44 between the target matter lumen 42 and lumen 38. Sufficient smoothing of the bifurcation and the like may also help maintain the smooth laminar flow. The blood (or other fluid) continues to flow as it is being filtered, and the filtering by waves 50 does not expose the blood flow to a large filter media surface area that might add to microparticulate embolization, generate additional microbubbles, or the like.

Microbubbles 54 tend to collect between peaks of waves 50, so that the microbubbles may be moved laterally across the bloodflow path as the waves propagate. The wavelength and power of waves transmitted by transmitter 30 will preferably be sufficiently low to avoid cavitation or damage to the blood, and specific power and wavelengths for a particular conduit may be determined by appropriate parametric studies. Typical filters will have powers of from about 20 to about 50 W, with frequencies of from about 400 kHz to about 4.5 MHz. Transducers capable of handling 250 watts at 15 volts rms (or greater, optionally being 100 volts rms) and 10 amps may be suitable for some embodiments. Including a suitable material in the conduit where the waves strike the luminal wall can inhibit reflections, as can maintaining the angle between the impinging waves and the luminal surface sufficiently close to about 90°.

An alternative filter 60 can be understood with reference to FIGS. 4 and 4A through 4G. Filter 60 again includes a conduit with a lumen providing fluid communication between an input 62 and an output 64. In this embodiment, the conduit comprises a series of plates having channels therein, with the channels together defining a lumen 66 when the plates are stacked together. Lumen 66 once again follows a path 68 similar in form to Mobius strip, with the luminal walls presenting an elongate, relatively thin cross-section adjacent transmitter 30.

Figure 4:
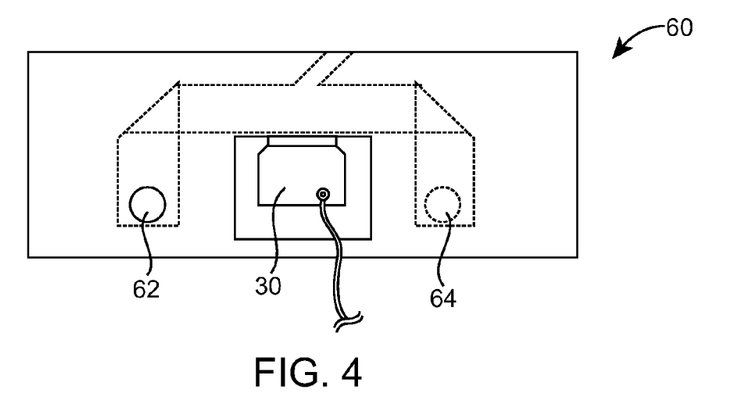
FIG. 4 is a side view of an alternative embodiment of a biological fluid filter for use in the system of FIG. 1.
Figure 4A:
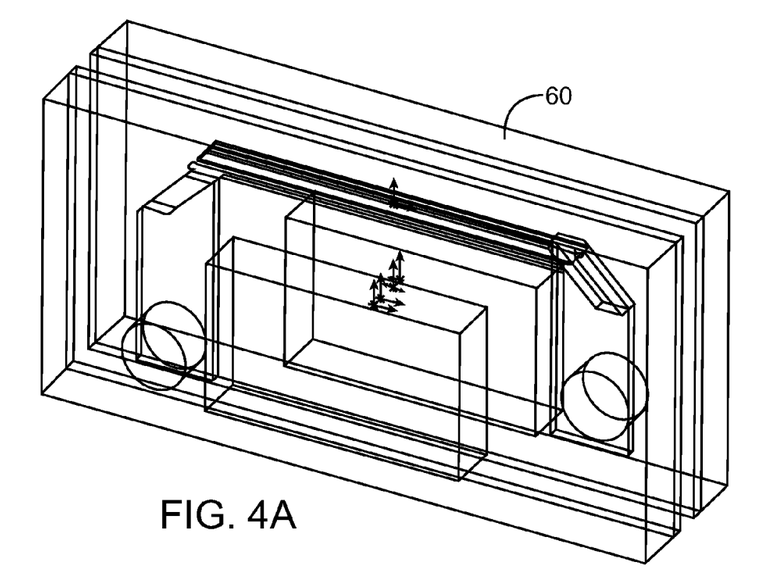
FIGS. 4A and 4B are a prospective view and end view, respectively, of the filter conduit structure of the filter of FIG. 4.
Figure 4B:
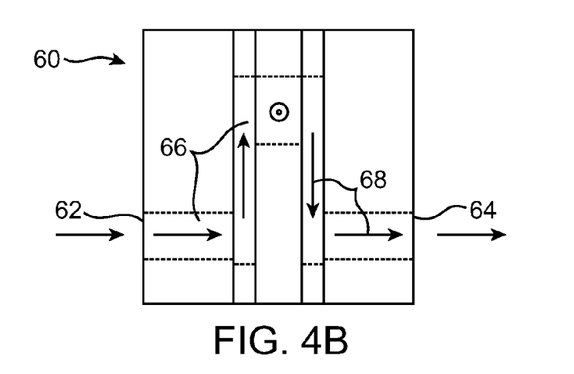
Figure 4C:
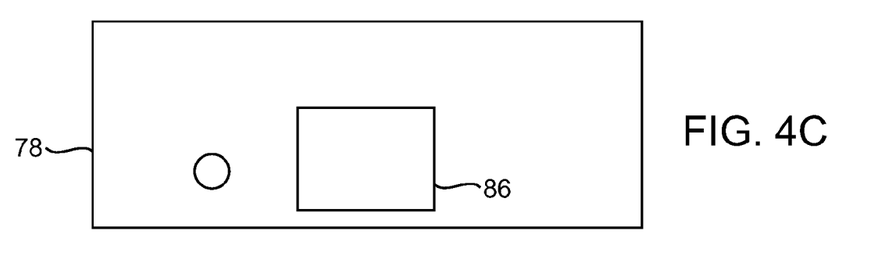
FIGS. 4C through 4G are side views showing the structures of plates that can be stacked together to form the filter of FIG. 4.
Figure 4D:
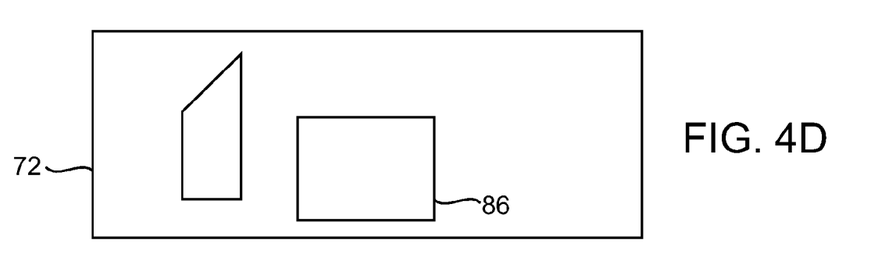
Figure 4E:
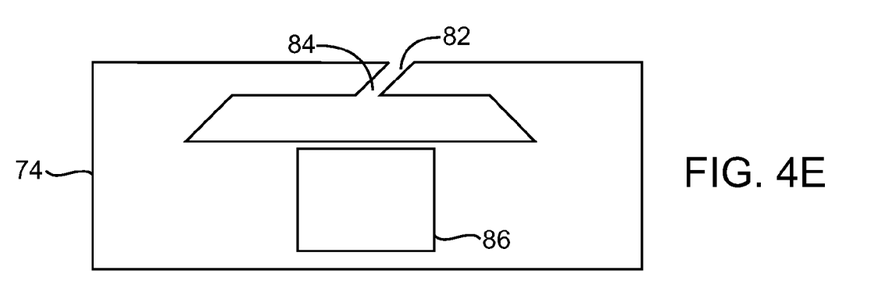
Figure 4F:
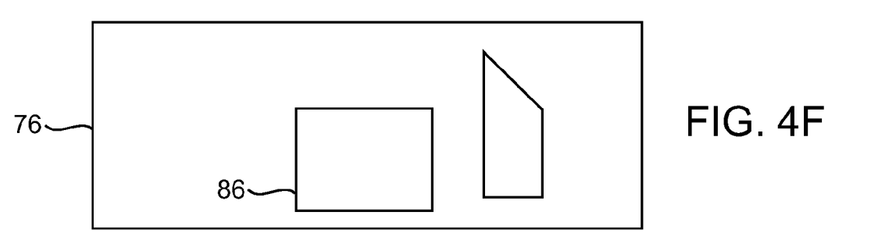
Figure 4G:
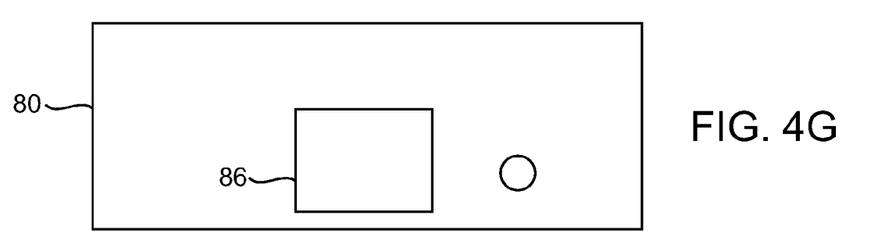

The lumen path 68 within filter 60 can be understood by reviewing the individual channels of the plates from which the conduit is formed (see FIGS. 4C-4G), and by comparing those channels to the side, end, and perspective view of FIGS. 4, 4B and 4A, respectively. The conduit of filter 60 includes three plates 72, 74 positioned between two end plates 78, 80. Central plate 74 may also define the target matter lumen 82 and port 84. An opening 86 in each of the plates accommodates ultrasound transmitter 30. As can be seen in FIG. 4A, ultrasound transmitter 30 may optionally be acoustically coupled to the flow within the lumen by providing an opening in the conduit.

Figure 5:
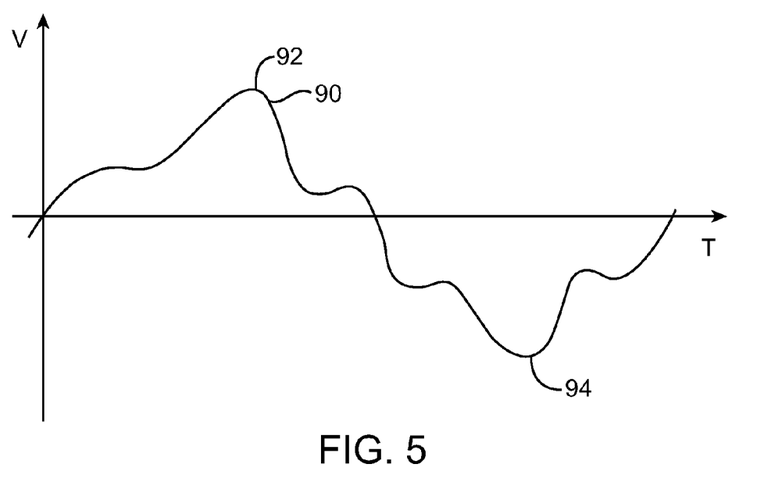
FIG. 5 schematically illustrates a complex waveform having a plurality of changes in curvature sign between adjacent maximum and minimum amplitudes.
Figure 5A:
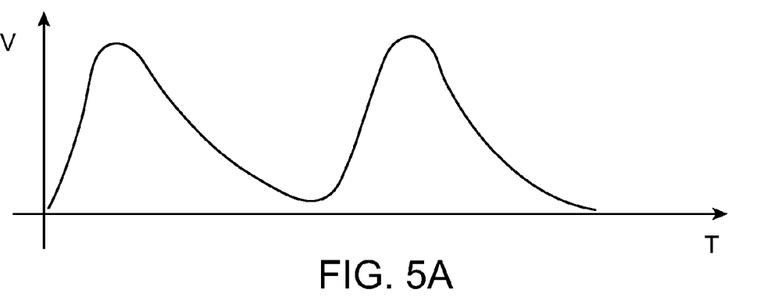
FIG. 5A schematically illustrates an alternative waveform having a 10% energized pulse duty cycle for driving the ultrasound transducer.

Referring now to FIG. 5, the general characteristics of a waveform which may enhance filtering efficacy when applied by driver 18 to the ultrasound transmitter of filter 16 (see FIG. 1) is schematically illustrated. The curvature of waveform 90 varies between a positive curvature (second derivative of greater than 0) and a negative curvature (second derivative of less than 0) a plurality of times within a single cycle between a maximum amplitude 92 and a minimum amplitude 94. An alternative waveform which may enhance filtering efficacy is illustrated in FIG. 5A, with the waveform here having a 10% duty cycle. Sign waves, square waves, triangular waves, and other standard shapes may be used in some embodiments, but not provide the same microbubble filtering efficacy, even though waveform 90 may be generated without providing true resonance in the driving circuit as is typically desired for power circuits.

Figure 6:
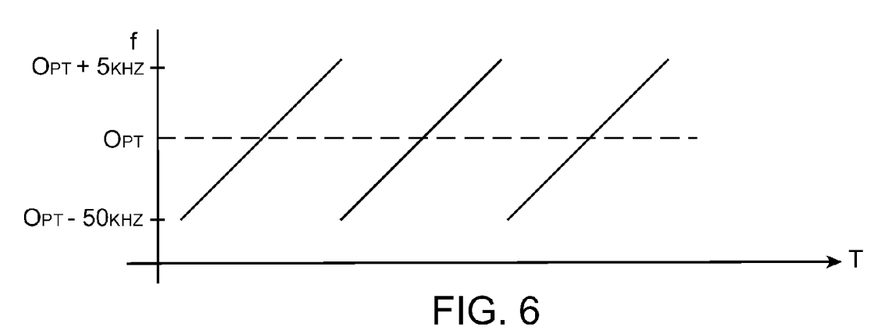
FIG. 6 schematically illustrates sweeping the driving frequency of the transducer so as to inhibit the formation of standing waves within the filtering conduit.

Referring now to FIG. 6, driving the transducer with a frequency f which changes over time may inhibit the formation of standing waves. Such standing waves might otherwise interfere with filtering of target matter from the fluid flow. A variety of changes, alterations, or variations to the frequency might be employed, with the exemplary sweeping of the frequency comprising a smooth and gradual change from about 50 kHz below an optimized or desired filtering frequency Opt to about 50 kHz above the optimized or desired filtering frequency. Each sweep may take between about 0.01 sec and about 50 sec. Incremental changes in frequency might also be employed in other embodiments.

While the exemplary embodiments have been described in some detail, by way of example and for clarity of understanding, those of skill in the art will recognize that a variety of modification, adaptations, and changes may be employed. For example, multiple ultrasound filter stages may be used to decrease blood or other filtered fluid loss. High density target materials might be filtered from lower density fluids using gravity assistance by positioning the target material port below the lumen. A wide variety of other changes might similarly be made. Hence, the scope of the present invention should be limited solely by the appending claims.

What is claimed is:

1. A method for filtering a biological fluid, the method comprising:

flowing the fluid along a fluid flow path defined by a lumen of a conduit, the lumen defining an elongate cross-section across the flow path;

driving target matter from within the flowing fluid toward a target matter port by directing ultrasound or acoustic waves from a transmitter across the fluid flow path and along the elongate cross-section of the lumen;

sweeping a frequency of the waves so as to enhance filtering of the target matter from the fluid flow path;

maintaining laminar flow of the fluid along the transmitter via a shape of the lumen; and removing the target matter from the fluid flow path through the port.

2. The method of claim 1, wherein the driving of the target matter from the flowing fluid is assisted by gravitational separation of the fluid, the target matter differing significantly in density from the fluid.

3. The method of claim 1, further comprising balancing fluid path resistance across the lumen by providing at least 180 degrees of axial twist along the flow path.

4. The method of claim 1, further comprising inhibiting filtration-degrading reflection of the waves within the lumen defining the path by at least one of:

matching an acoustic impedance of a material defining a lumen wall to an acoustic impedance of the fluid flow; or maintaining a reflection-inhibiting angle between the waves and the lumen wall.

5. The method of claim 1, wherein the conduit comprises a first disposable conduit and further comprising inhibiting contamination between the fluid and another biological fluid to be filtered by replacing the first disposable conduit with a second disposable conduit, disposing of the first disposable conduit, and filtering the other fluid by transmitting the waves from the transmitter through the second disposable conduit.

6. The method of claim 1, further comprising driving the transmitter with a non-standard alternating current waveform tailored to enhance target matter removal.

7. The method of claim 1, further comprising driving the transmitter with a frequency that changes so as to inhibit formation of standing waves.

8. The method of claim 1, wherein the target matter comprises gas bubbles and the fluid flow comprises blood flow.

9. The method of claim 1, wherein the conduit defining the fluid path has an input end and an output end, wherein the fluid flow across the elongate cross-section is balanced by an axial twist of the cross section between the input end and the output end of at least 180 degrees, wherein the fluid and the target matter flow in via the input end, wherein the fluid flows out the output end, and wherein the driving of the target matter by the waves directs the target matter toward the port so as to separate the target matter out of the flow of fluid passing through the output end.

10. A method for filtering blood, the method comprising:

flowing the blood through a conduit having an input end, an output end, and a lumen defining a laminar fluid flow path therebetween;

driving bubbles from within the blood toward a port disposed along the laminar fluid flow path between the input end and the output end by directing ultrasound or acoustic waves having a sweeping frequency across the laminar fluid flow path so as to separate the bubbles out of the flow of blood passing through the output end; and removing the bubbles from the conduit through the port.

11. The method of claim 10, wherein the lumen has an elongate cross-section and the fluid flow comprises a laminar flow, and further comprising balancing fluid path resistance across the lumen by providing at least 180 degrees of axial twist of the elongate cross-section along the conduit.

12. The method of claim 10, wherein the bubbles comprise gas microbubbles, and wherein the port is near the top of the lumen so that gravitational separation assists in removal of the microbubbles.

\* \* \* \* \*